United States Patent
Casu' et al.

(10) Patent No.: US 6,562,562 B2
(45) Date of Patent: May 13, 2003

(54) PROCEDURE FOR PARTIAL LIVER RESECTION IN NONHUMAN PRIMATES

(75) Inventors: Francesco Casu', Gallarate (IT); Claudio Bernardi, Milan (IT); Luciano Dho, Parabiago (IT); Bruno Rosa, Motta Visconti (IT)

(73) Assignee: Pharmacia & Upjohn S.p.A., Milan (IT)

(*) Notice: Subject to any disclaimer, the term of this patent is extended or adjusted under 35 U.S.C. 154(b) by 62 days.

(21) Appl. No.: 09/796,529

(22) Filed: Mar. 2, 2001

(65) Prior Publication Data

US 2001/0055805 A1 Dec. 27, 2001

Related U.S. Application Data

(60) Provisional application No. 60/188,199, filed on Mar. 10, 2000.

(51) Int. Cl.$^7$ .................................................. L12N 5/00
(52) U.S. Cl. .................... 435/1.1; 435/363; 435/370; 604/540
(58) Field of Search ......................... 435/1.1, 370, 363; 604/540

(56) References Cited

U.S. PATENT DOCUMENTS 4,164,566 A * 8/1979 Provost et al.

FOREIGN PATENT DOCUMENTS

EP 0028987 A2 * 5/1981

* cited by examiner

Primary Examiner—Leon B. Lankford, Jr.
(74) Attorney, Agent, or Firm—Birch, Stewart, Kolasch & Birch, LLP

(57) ABSTRACT

A surgical procedure (partial hepatectomy) in the nonhuman primate allows repeated removal of large liver tissue samples from a single animal for the preparation of liver tissue slices and primary cell culture of hepatocytes. The open biopsy procedure, alternating non-anatomic and anatomic partial liver resection monthly on the same liver lobe, follows a surgical protocol allowing animal welfare, survival, and multiple sampling (at least 8) from the same animal, thus reducing considerably the number of animals needed for research purposes.

8 Claims, No Drawings

PROCEDURE FOR PARTIAL LIVER RESECTION IN NONHUMAN PRIMATES

This application claims the benefit of provisional Patent Application 60/188,199, which was filed on Mar. 10, 2000.

FIELD OF THE INVENTION

The present invention provides a new surgical procedure of partial hepatectomy, in nonhuman primates. More particularly, the present invention provides an open biopsy procedure, alternating non-anatomic and anatomic partial liver resection on a liver lobe.

BACKGROUND OF THE INVENTION

The first relevant anatomic studies of the liver emerged with the endeavors of Herophilus and Erasistratus between 310 and 280 B.C. However, it was not until after the development of anesthesia and antisepsis that the first formal hepatic resections were performed in human medicine during late 1800's. After a burst of pioneering activity from 1880 to 1910 (1, 2), little progress was made until World War II. In the last 50 years, remarkable advances in the surgical techniques of human liver resections were made (3, 4, 5) based on the increasing knowledge of the anatomy of the liver. Accurate and safe surgical procedures have been implemented to intervene at the level of the liver parenchyma and bile ducts with increased safety margin and optimal clinical outcomes.

Hepatic resection, or hepatectomy, is defined as the removal of a liver segment or a complete liver lobe. Partial hepatic tissue resection is immediately followed by the regeneration of the liver parenchyma within a few weeks (6, 7, 8, 9, 10, 11, 12). The regenerative response of the liver is proportional the amount of tissue removed leading eventually to the restoration of the original size and with adaptation to whole body size if liver from large animals are transplanted into small animals of the same species.

In human surgery, hepatectomies are classified as total when the organ is used for liver transplantation and partial when, e.g., areas of isolated primary or secondary metastasis are removed. Partial hepatectomies are subdivided in anatomic and non-anatomic resections. Anatomic resections are defined by the vascular structure, while non-anatomic resections are performed at the level of the liver parenchyma. At least six different techniques for human hepatectomy have been described in the literature (6).

In veterinary medicine and research, liver biopsy is an important diagnostic tool in evaluating hepatic morphology, assessing molecular and biochemical properties of the liver for both clinical and research purposes. Indications for partial liver removal include localized masses such as abscesses or neoplasia, trauma, vascular alterations, viral hepatitis, and research. The techniques available for partial liver resection can be classified into two major groups: open and closed liver biopsies (13).

The closed biopsy procedures are performed by percutaneous needle biopsy using a transabdominal or transthoracic approach. Closed liver biopsy can be performed rapidly under local anesthesia and is best suited for multisampling. However, it is limited by the small sample size (about 100 mg) and numerous complications such as puncture of the gallbladder or adjacent organs and bacterial peritonitis that can occur due to the blinded fashion by which this technique is performed (13, 14, 15, 16). A better accuracy in sample collection can be achieved by combining a keyhole technique to needle biopsy puncture (13, 14). In this semi open technique, a cranial ventral midline incision is performed to allow localization and mobilization of the liver lobes by direct digital palpation. However, even if the risk of aberrant puncture can be decreased, this technique offers the disadvantage of being still limited by its small sample size.

Open techniques for partial liver resection have been previously described in rats, dogs and nonhuman primates (13, 17, 18, 19, 20, 21, 22, 23). Following the terminology used in human liver surgery, open biopsies in animals are used to perform partial non-anatomic liver resections. These techniques can be categorized into four major groups: punch biopsy, wedge resection, finger fractures, and ligature fractures.

The punch biopsy uses Keys cutaneous biopsy punch for collecting of small, superficial samples in essentially any location on the liver surface (13).

Wedge liver resection can be used to remove larger areas located on the edge of the liver lobes. However, this technique involves the application of a horizontal mattress, using interlapping sutures along the line that will give the desired piece of liver. This procedure is invasive but allows the dissection of relatively large liver samples (50–100 grams). The potential risk of developing post-surgery intrahepatic hematomas due to the significant amount of suture material left deep with the hepatic parenchyma has been underlined (13, 21).

One of the most commonly used procedures for partial lobectomy of large sections of the liver is the finger fracture technique. In this technique, the portion of hepatic tissue to be removed is fractured by the fingers and the difference in resistance between the liver parenchyma and the intrahepatic ducts and vessels is readily apparent, thus making them easily identified. Once the hepatic segment has been crushed away from the ducts and vessels, they are clamped, ligated and severed controlling thereby hemorrhage and bile leakage (13, 15, 18, 20, 24). However, in rhesus macaques studies have shown that extensive blunt dissection causes the release of proteolytic enzymes into the circulation resulting in postoperative P02 depression (20).

The ligature fracture technique has been described has the quickest and most simple method to collect large biopsy liver samples (15, 23). In both African green and cynomolgus monkeys, the ligature technique was used to obtain multiple large (2 to 4 gr) liver biopsy samples. This technique was applied 195 times in 84 animals using three different surgical approaches indicating that 2 to 3 partial liver resections can be performed on the same animal. However, data indicated that serum alanine aminotransferase (ALT) concentration undergoes a transient but significant elevation in association with acute hepatocellular damage. Nolan and Conti (21) described a procedure for removing large (10–20 gr) liver samples in chimpanzees using an automatic stapling device for cell culture experiment purposes. Three biopsies were performed on the same animal but from areas not involved in the previous biopsy.

However none of these studies addressed a suitable method to perform multiple (more than 3) liver biopsies in nonhuman primates in which approximately 20 gr of tissue would be removed in each instance for tissue slices and cell culture purposes. In addition, a procedure allowing more than one intervention on the same liver lobe has not been described.

The 3R's principle (refining, reducing, replacing) is one of the most important and leading issue in Laboratory Animal Science. In vitro testing is a fundamental tool to optimize, reduce, refine, and replace the use of laboratory animals, particularly working with nonhuman primates.

An objective of this invention is to provide a new surgical procedure of partial hepatectomy in the nonhuman primate allowing repeated removing of liver tissue samples from the same animal for the preparation of liver tissue slices and cell culture of hepatocytes.

SUMMARY OF THE INVENTION

The new surgical procedure of partial hepatectomy in the nonhuman primate described in this invention allows repeated removal of large (about 20 gram) liver tissue samples from a single animal for the preparation of liver tissue slices and primary cell culture of hepatocytes. This open biopsy procedure, alternating non-anatomic and anatomic partial liver resection monthly on the same liver lobe, follows a surgical protocol allowing animal welfare, survival, and multiple sampling (at least 8) from the same animal. This procedure for multiple partial liver resection thus reduces considerably the number of animals needed for research purposes. This new surgical procedure is simple and safe. It does not produce pain, uncontrollable hemorrhage, anemia, bile leakage into the peritoneal cavity, dehydration, or hepatic insufficiency.

In more detail, the procedure developed and described herein preferably consists in the application of alternative non-anatomic and anatomic hepatectomy resection for eight removals of liver tissue sections from the same animal. Each operation is performed monthly on the same animal. The procedure consists in eight surgery steps alternating liver lobe clamping and resection of a segment of parenchyma without the use of ligature fracture followed after one month by an intervention on the same liver lobe clamping the vascular pedoncule for total lobectomy. These two alternative steps were repeated on the left lateral, right lateral, left central, and right central liver lobes, respectively.

Thus, the present invention provides a surgical procedure of partial hepatectomy in a nonhuman primate, which comprises repeated removal from the same animal of large liver tissue samples suitable for the preparation of liver tissue slices and primary cell culture of hepatocytes.

The surgical procedure herein preferably follows an open biopsy procedure following a protocol alternating non-anatomic and anatomic partial hepatic resection for eight removals of liver tissue sections from the same animal.

A particularly preferred embodiment of the surgical procedure of the present invention comprises the sequential steps of, (A) on the left lateral liver lobe, clamping and resectioning a segment of parenchyma without the use of ligature fracture followed after one month by resection of the remaining liver lobe after clamping and ligation of the vascular pedoncule, (B) on the right lateral liver lobe, clamping and resectioning a segment of parenchyma without the use of ligature fracture followed after one month by resection of the remaining liver lobe after clamping and ligation of the vascular pedoncule, (C) on the left central liver lobe, clamping and resectioning a segment of parenchyma without the use of ligature fracture followed after one month by resection of the remaining liver lobe after clamping and ligation of the vascular pedoncule, and (D) on the right central liver lobe, clamping and resectioning a segment of parenchyma without the use of ligature fracture followed after one month by resection of the remaining liver lobe after clamping and ligation of the vascular pedoncule.

Thus this invention provides a method of promoting animal welfare, survival, and reduction in the number of animals employed for research purposes on liver tissue slices and primary culture of human hepatocytes.

DETAILED DESCRIPTION OF THE INVENTION

Animals

Males, 5 years old Cynomolgus monkeys (*Macaca fascicularis*), with a body weight of about 6 kg were used to perform multiple partial liver resection surgery for the preparation of primary culture of hepatocytes.

The animals were housed individually in stainless steel cages (67×63×76 cm) at a room temperature of 20–22° C., with a relative humidity of 55±5% and a 12/12 hours light/dark cycles. The animals were fed with a standard primate diet (Altromin A®) received fresh fruit and water ad libitum. Experiments were performed in compliance with the Legislative Decree dated Jan. 27, 1992, N° 116 enforcing the ECC Instruction n. 86/609/ECC concerning the protection of animals used for experimental or other scientific purposes (25) and the EC Council Instruction dated Nov. 24, 1986, concerning legislative requirements for European Countries related with the protection of animals used for experimental or other scientific purposes (86/609/ECC) (26).

Before each operation, animals were fasted for 24 hours and received water ad libitum. They were tranquilized giving intramuscularly Aceptromazine maleate (Prequillan®) at 0/2 mg/kg. Thereafter, animals were sedated with Ketamine hydrochloride (Ketavet 100®) and Xilazine hydrochloride (Rompun®) given both intramuscularly at 10 and 0.5 mg/kg, respectively. The animals were positioned in dorsal recumbency on the surgical table. The abdominal area was prepared and draped for aseptic surgery.

During the operation, the animals were given an electrolyte sterile solution balanced with glucose 20% (20% Glucose Solution®) at 20 ml/kg subcutaneously, Buprenorphine hydrochloride (Temgesic®) at 0.01 mg/kg intramuscularly eight hourly as analgesic therapy and Enrofloxacin (Baytril®) at 5 mg/kg subcutaneously b.i.d. as antibiotic therapy.

Post-surgery, on Day 1 the animals received fresh fruit and water ad libitum and from Day 2 the standard primate diet.

Surgical Procedure

A midline laparotomy incision was made extending from the xiphoid cartilage caudally for approximately 20 cm. The incision was continued through the fascia, muscle, and peritoneum. The edges of the incision were protected with laparotomy sponges and retracted with a Gosset retractor. The liver was then exposed.

The procedure for multiple partial liver resection was performed in eight steps. In each step, amputation was achieved in a few minutes. Before each liver lobe resection described below, adhesions were carefully removed.

STEP 1: the left lateral liver lobe was localized and the segment of the liver to be removed was selected. Clamping of the segment was performed by using a curved vascular clamp, the convex part of the clamp being directed towards the hilum. Thereafter, the segment was carefully dissected slipping the scalpel along the concave part of the clamp. After 3 minutes, the clamp was removed and hemorrhage was carefully controlled. If residual bleeding from the remaining raw surface of the left lateral liver lobe occurred, electrocautery was used. Washing of the liver and of the abdominal cavity was performed with a sterile saline solution maintained at 37° C. The peritoneum, muscle wall, and fascia were then closed with a non-interrupted suture using 2-0 polyglycolic acid (Vicryl®, Ethicon). Interrupted sutures were performed to close the subcutis tissue using 3-0 polyglycolic acid (Vicryl®, Ethicon) and the skin using 2-0 silk (Perma-Hand®, Ethicon) respectively.

STEP 2: a second partial liver resection in the same animals was performed one month after the first operation. The remaining part of the left lateral liver lobe was localized and adhesions, if present, were removed. The vascular structure was localized, clamped and ligated using 2-0 polypropylene suture (Prolene®, Ethicon) in two distinct sites above and below the clamp, respectively. The liver segment was then excised.

Washing of the liver and of the abdominal cavity was performed with a sterile saline solution maintained at 37° C. The peritoneum, muscle wall and fascia were then closed with a non-interrupted suture using 2-0 polyglycolic acid (Vicryl®, Ethicon). Interrupted sutures were performed to close the subcutis tissue and the skin using 3-0 polyglycolic acid (Vicryl®, Ethicon) and 2-0 silk (Perma-Hand®, Ethicon), respectively.

STEP 3 TO STEP 8: one month interval period was observed between each operation for the successive partial liver resections in the same animals. Using the experimental conditions described in Step 1, segments from the right lateral, left central and right central liver lobes were removed in Steps 3, 5, and 8, respectively. Experimental conditions described in Step 2 were used to excise the remaining right lateral, left central, and right central liver lobes in Steps 4, 6, and 8, respectively.

Results

No spontaneous death occurred during the study. The three animals on which multiple liver biopsies have been performed had uneventful recoveries after each operation step. Two animals were sacrificed two weeks after the last intervention and one animal is still alive in welfare conditions sixth month after the fourth operation for partial liver resection.

Clinical signs of distress and pain were not observed. The animals showed normal behavior from the first postoperative day after each intervention. Food consumption was normal from the second postoperative day and body weight losses were not observed.

During each intervention, the animals demonstrated an optimal intraperitoneal hemostasis without occurrence of uncontrollable hemorrhage and no suture of the liver parenchyma was needed. The accurate washing of the liver and the abdominal cavity after each intervention allowed reducing considerably the formation of adhesions and easy reintervention on the same liver lobe after a period of one month. Gross evaluation of the liver performed during each intervention demonstrated organized regeneration of the liver tissue. No anemia and release of bile into the peritoneal cavity was observed postoperatively after each intervention.

Serum concentrations of alanine aminotransferase (ALT), aspartate aminotransferase (AST), direct and total bilirubin were determined during the postoperative period to assess potential hepatic dysfunction. The animals demonstrated a mild and transient increase mainly in ALT and AST in the second and third post-operative day after each operation but after 10 days recovery was observed. Total plasma protein remained within the normal range in each animal after each intervention indicating that no dehydration occurred. Optimal primary cultures of hepatocytes were obtained after each partial liver lobe resection with a cell survival of more than 75% in each preparation.

Summary

The new surgical procedure of partial hepatectomy in the nonhuman primate described in this invention allows repeated removing of large (about 20 gram) liver tissue samples from the same animal for the preparation of liver tissue slices and primary cell culture of hepatocytes. This open biopsy procedure, alternating non-anatomic and anatomic partial liver resection monthly on the same liver lobe, follows a surgical protocol allowing animal welfare, survival and multiple sampling (at least eight) from the same animal. This procedure for multiple partial liver resection allowed reducing considerably animal number for research purposes. This new surgical procedure is simple and safe, as it did not produce uncontrollable hemorrhage, anemia, bile leakage into the peritoneal cavity, dehydration, and hepatic insufficiency.

The above description of the present invention is for illustrative purposes only. Many variations and modifications of the present invention that will also enable attainment of the benefits of the invention will readily occur to those skilled in the art.

REFERENCES

The entire disclosure of each of the literature articles cited in this application is hereby expressly incorporated herein by reference.

1. McClusky D. A. $3^{rd}$, Skandalakis L. J., Colborn G. L. and Skandalakis J. E., 1997: Hepatic surgery and hepatic surgical anatomy: historical partners in progress. World J. Surg., 21(3):330–442.
2. Foster, J. H., 1991: History of liver surgery. Arch.Surgery, 126(3):381–387.
3. Gans H., 1955: Introduction to Hepatic Surgery. Amsterdam, London, Elsevier Publishing Co.
4. Tien-Yu L, Kuang-Yung H., Chen-Min H., and Chi-Sen. C., 1958: Study on lobectomy of the liver: a new technical suggestion on hemihepatectomy and reports of 3 cases of primary hepatoma treated with total left lobectomy of the liver. J. Formosan Med. Assoc., 57:74.
5. Tien Y. L., Kai-Mo C. and Tang Kue L., 1960. Total right lobectomy for primary hepatoma. Surgery, 48:1048–1060.
6. Broelsch C. E., 1992: Atlas of Liver Surgery. Ed. Churchill Livingstone, London, UK.
7. Michalopoulos G. K. and DeFrances M. C., 1997: Liver Regeneration. Science, 276:60–66.
8. Taub R., 1996: Liver Regeneration in Health and Disease. Clinics in Laboratory Medicine, 16(2): 341–360.
9. Freeman T. L., Hao Q. Ngo and Mailliard M. E., 1999: Inhibition of system A amino acid transport and hepatocyte proliferation following partial hepatectomy in the rat. Hepatology 2:437–444.
10. Francavilla A., Ove P., Polimeno L., Coetzee M., Makowka L., Barone M., Van Thiel D. H., and Starzl T. E., 1988: Transplantation Proceedings, 20:494–497.
11. Gans H., Mon K., Matsumoto K. and Tan B. H., 1974: Evaluation of Starzl T. E., Fung J., Todo S., Demetris A. J., Marino I. R., Doyle H., Zeevi A., Warty V., Michaels M., Kusne S., Rudert W. A. and Trucco M., 1993: baboon-to-human liver transplantation. Lancet, 341 (8837):65–71.
12. Kawasaki S., Makuuschi M., Ishizone S., Matsunani H., Terada M. and Kawarazaki H., 1992: Liver regeneration in recipients and donors after transplantation. Lancet, 339:580–581.
13. Walshaw R., 1985: Liver and biliary system: surgical diseases. In D. H. Slatter (Ed.), Textbook of small animal surgery. Vol.1, W. B. Saunders, Philadelphia, PA.
14. Osborne C.A. et al., 1974: Liver Biopsy. Vet. Clin. North Am., 4:333.
15. Furneaux R., 1975: Surgical techniques for the spleen and the liver. Vet. Clin. North Am., 5:562.
16. Feldman E. C. and Edwards D. F., 1983: Closed biopsy techniques of the liver. In M. J. Bojrad (Ed.), Current 17. Putnam C. W. and Starzl T. S., 1977: Simplified biopsy of the liver in dogs. Surgery, Gynecology & Obstetrics 144:759.
18. Dingwall J. S., de Boer J., 1970. A new technique for liver resection in the dog. Journ. of small Anim. Pract. 7:429–433.
19. Voss W. R., 1970: Primate liver and spleen biopsy procedures. Laboratory Animal Care 5:995–997
20. the effects of finger fracture technique used in hepatic resection. Surgery, Gynecology & Obstetrics, 138:885–890.
21. Nolan T. E. and Conti P. A., 1980: Liver wedge biopsy in chimpanzees (Pan troglodytes) using an automatic stapling device. Laboratory Animal Science, 3:578–580.
22. Eichberg J. W., 1985: Liver wedge biopsy in nonhuman primates. J. Med. Primatol, 14:165–168.
23. Talcott M. R. and Tysko R. C., 1991. Partial lobectomy via a ligature fracture technique: a method for multiple hepatic biopsies in nonhuman primates. Laboratomy Animal Scienc, 41(5):476–480.
24. Breznock E. M., 1983: Surgery of hepatic parenchyma and biliary tissues. In M. J. Bojrad (Ed.), Current Techniques in Small Animal Surgery II, Lea & Fibiger, Philadelphia, Pa.
25. Legislative Decree dated Jan. 27, 1992, N° 116 enforcing the ECC Instruction n. 86/609/ECC concerning the protection of animals used for experimental or other scientific purposes. In: Official Gazette of the Italian Republic n.40, issued in Rome on Feb. 18, 1992.
26. EC Council Instruction dated Nov. 24, 1986, concerning legislative requirements for European Countries related with the protection of animals used for experimental or other scientific purposes (86/609/ECC). In ECC Official Gazette n. L 358/27, Dec. 18, 1986.

What is claimed is:

1. A surgical procedure of partial hepatectomy in a nonhuman primate which comprises repeated removal from the same animal of large liver tissue samples suitable for the preparation of liver tissue slices and primary cell culture of hepatocytes, wherein each sample subsequent to the first sample is removed a month subsequent to the removal of the previous sample.

2. A surgical procedure of partial hepatectomy in a nonhuman primate, said procedure comprising repeated removal from the same animal of liver tissue samples weighing about 20 grams and suitable for the preparation of liver tissue slices and primary cell culture of hepatocytes.

3. The surgical procedure of claim 1 comprising alternating non-anatomic and anatomic partial hepatic resection for eight removals of liver tissue (sections from the same animal.

4. A surgical procedure of partial hepatectomy in a nonhuman primate, said procedure comprising repeated removal from the same animal the sequential steps of on the left lateral liver lobe, clamping and resectioning a segment of parenchyma without the use of ligature fracture followed after one month by resection of the remaining liver lobe after clamping and ligation of the vascular pedoncule, on the right lateral liver lobe, clamping and resectioning a segment of parenchyma without the use of ligature fracture followed after one month by resection of the remaining liver lobe after clamping and ligation of the vascular pedoncule, on the left central liver lobe, clamping and resectioning a segment of parenchyma without the use of ligature fracture followed after one month by resection of the remaining liver lobe after clamping and ligation of the vascular pedoncule, and on the right central liver lobe, clamping and resectioning a segment of parenchyma without the use of ligature fracture followed after one month by resection of the remaining liver lobe after clamping and ligation of the vascular pedoncule.

5. A method of promoting animal welfare, survival, and reduction in the number of animals employed for research purposes on liver tissue slices and primary culture of human hepatocytes, said method comprising practicing the procedure of claim 1.

6. A method of reducing the number of animals employed for research purposes on liver tissue slices and primary culture of human hepatocytes, said method comprising practicing the procedure of claim 2.

7. A method of reducing the number of animals employed for research purposes on liver tissue slices and primary culture of human hepatocytes, said method comprising practicing the procedure of claim 3.

8. A method of reducing the number of animals employed for research purposes on liver tissue slices and primary culture of human hepatocytes, said method comprising practicing the procedure of claim 4.

* * * * *